US006316023B1

(12) United States Patent
Asmussen et al.

(10) Patent No.: US 6,316,023 B1
(45) Date of Patent: *Nov. 13, 2001

(54) TTS CONTAINING AN ANTIOXIDANT

(75) Inventors: Bodo Asmussen, Bendorf-Sayn; Michael Horstmann, Neuwied, both of (DE); Kai Köpke, Triengen (CH); Henricus L. G. M. Tiemessen, Weil-Haltingen (DE); Steven Minh Dinh, Briarcliff Manor; Paul M. Gargiulo, New York, both of NY (US)

(73) Assignees: Novartis AG, Basel (CH); LTS Lohmann Therapie-Systeme GmbH, Neuwied (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/747,519

(22) Filed: Dec. 20, 2000

Related U.S. Application Data

(63) Continuation of application No. 09/291,498, filed on Apr. 14, 1999, which is a continuation-in-part of application No. PCT/EP99/00078, filed on Jan. 8, 1999.

(30) Foreign Application Priority Data

Jan. 12, 1998 (GB) ........................................ 9800526

(51) Int. Cl.[7] ........................................ A61K 9/70

(52) U.S. Cl. ........................ 424/449; 424/448; 602/57; 602/60; 604/290; 604/305; 604/307

(58) Field of Search ........................ 424/449, 448; 602/57, 60; 604/290, 305, 307

(56) References Cited

U.S. PATENT DOCUMENTS 4,948,807 * 8/1990 Rosin et al. ........................ 514/484
5,344,656 * 9/1994 Enscore et al. ........................ 424/448
5,462,745 * 10/1995 Enscore et al. ........................ 424/448
5,602,176 * 2/1997 Enz ........................ 514/490

FOREIGN PATENT DOCUMENTS 0 427 741 B1 * 5/1991 (EP) .
2 611 707 * 9/1988 (FR) .
89/12470 * 12/1989 (WO) .
98/30243 * 7/1998 (WO) .
98/31356 * 7/1998 (WO) .

OTHER PUBLICATIONS

Schneider, J Clin Psychiatry, (suppl 14), "New Therapeutic Approaches to Alzheimer's Disease", vol. 57, pp 30–36 (1996).

Sano, et al, The New England Journal of Medicine, "A Controlled Trial of Selegiline, Alpha–Tocopherol, or Both as Treatment for Alzheimer's Disease", vol. 336, No. 17, pp. 1216–1222 (1997).

Schneider et al., Am J Psychiatry, "A Double–Blind Crossover Pilot Study of I–Deprenyl (Selegiline) Combined With Cholinesterase Inhibitor in Alzheimer;'s Disease", vol. 150, No. 2, pp. 321–323 (1993).

Sunderland, et al., International Psychogeriatrics, "A Strategy of "Combination Chemotherapy" in Alzheimer's Disease: Rationale and Preliminary Results with Psysostigmine plus Deprenyl". Vol. 4 Suppl. 2, pp. 291–309 (1992).

* cited by examiner

*Primary Examiner*—S. Mark Clardy
*Assistant Examiner*—Michael A. Williamson
(74) *Attorney, Agent, or Firm*—John D. Thallemer

(57) ABSTRACT

Pharmaceutical composition comprising (S)-N-ethyl-3-[1-dimethylamino)ethyl]-N-methyl-phenyl-carbamate in free base or acid addition salt form and an antioxidant. Said pharmaceutical compositions may be delivered to a patient using a transdermal delivery device.

9 Claims, No Drawings

TTS CONTAINING AN ANTIOXIDANT

This application is a continuation of U.S. application Ser. No. 09/291,498, filed Apr. 14, 1999, which is a continuation-in-part of International Application No. PCT/EP99/00078, filed Jan. 8, 1999.

This invention relates to a pharmaceutical composition for systemic administration of a phenyl carbamate, e.g. by transdermal administration. In particular this invention relates to a pharmaceutical composition of the phenyl carbamate—(S)-N-ethyl-3-[1-dimethylamino)ethyl]-N-methyl-phenyl-carbamate—(hereinafter referred to as compound A) in free base or acid addition salt form as disclosed in published UK patent application GB 2 203 040, the contents of which are incorporated herein by reference.

Compound A is useful in inhibiting acetylcholinesterase in the central nervous system, e.g. for the treatment of Alzheimer's disease.

A transdermal composition in the form of a patch is described in Example 2 of GB 2,203,040 according to which compound A is mixed with two polymers and a plasticiser to form a viscous mass. This mass is applied to a foil which is cut into patches.

It has now been found after exhaustive testing that compound A is susceptible to degradation, particularly in the presence of oxygen. The transdermal composition described in GB 2203040 has been found to degrade, possibly by oxidative degradation, despite the formation of an occlusive polymer matrix around compound A and its storage in air-tight packaging.

The present applicant has found that stable pharmaceutical compositions comprising compound A can now be obtained, which show insignificant degradation of compound A over a prolonged time period, e.g. 2 years, as indicated by standard tests, e.g. stress tests.

In one aspect, the invention provides a pharmaceutical composition comprising Compound A in free base or acid addition salt form and an anti-oxidant.

The pharmaceutical compositions of the present invention show a reduction in degradation by-products in stress stability tests.

The pharmaceutical compositions of the invention may contain high amounts of compound A, e.g. from 1 to 40% by weight, e.g. 10–35%, more particularly 20–35%, e.g. 30%.

The compound A may be in any of a wide variety of pharmaceutical diluents and carriers known in the art. The diluent or carrier may contain trace amounts of free radicals without affecting the stability of the pharmaceutical composition of the invention.

The diluent or carrier is preferably one or more polymers, more preferably a hydrophilic polymer or polymers. In a preferred embodiment the diluent of carrier is selected from at least one polymer selected from acrylate polymers, and polymethacrylate polymers. The polymers preferably have a mean molecular weight of from about 50,000 to about 300,000 Daltons, e.g. 100,000 to 200,000 Daltons. The polymers preferably are capable of forming a film, thus to be compatible to the skin.

As a polymer one can mention in particular an acrylate co-polymer, e.g. co-polymers of butyl acrylate, ethyl hexyl acrylate and vinyl acetate. Preferably the polymer is cross-linked. A preferred acrylate polymer is one of the Durotak brand available from National Starch and Chemical Company, Zutphen, Holland, e.g. Durotak 87-2353 (hereinafter polymer A), 387-2051 or 387-2052 (hereinafter polymer D).

The diluent or carrier is preferably present in an amount of up to 90%, more preferably 70% by weight base on the total weight of the pharmaceutical composition.

The polymer, when a hydrophilic polymer, may conveniently take up water and is permeable to water, e.g. moisture from the skin, although the polymer may be insoluble in water. The polymer may swell and provide release of a large amount of pharmacologically active agent leading to a high concentration gradient of pharmacologically active agent between the skin surface and stratum corneum at a pH of from 4 to 7, preferably at skin pH, e.g. around 5.5. If desired such polymers may be soluble in organic solvents.

Examples of suitable polymers include polyacrylamide and its co-polymers, polyvinylpyrrolidone (PVP), vinyl acetate/vinyl alcohol co-polymers, polyvinyl alcohol (PVA) and derivatives, ethyl cellulose and other cellulose and starch derivatives.

Hydrophilic polyacrylates are preferred polymers. The polyacrylate may be substituted, e.g. a methacrylate. They may be commercially available acrylate/methacrylate co-polymers. Some or all of the acid groups may be esterified, e.g. with alkyl ($C_{1-10}$) groups, more particularly alkyl groups having 1 to 4 carbon atoms such as methyl or ethyl groups.

Examples of commercially available polymers of this type include:

1) Polymers of methacrylate containing alkyl ($C_{1-4}$) ester groups. Preferably the polymer matrix is a mixture of an acrylate polymer and a methacrylate polymer e.g. in a weight ratio of from 5:1 to 1:1, e.g. 4:1 to 2:1 e.g. 3:1, e.g. butylmethylacrylate and methylmethylacrylate. MW 20000, e.g. Plastoid B from Röhm, Darmstadt, Germany (hereinafter polymer B).
2) Polymers of acrylate and methacrylate esters containing methyl and ethyl neutral ester groups and trimethylaminoethyl cationic ester groups. Chloride ions may be present. Mean Molecular weight 150000 Daltons. Viscosity (20° C.), maximum 15 cP. Refractive index 1.380–1.385. Density 0.815–0.835 g/cm$^3$. Ratio of cationic ester groups to neutral alkyl groups 1:20 giving an alkali count of 28.1 mg KOH per gram polymer (Eudragit RL 100 Registered Trade Mark available from Röhm) or 1:40 giving an alkali count of 15.2 mg KOH per gram polymer (Eudragit RS 100 Registered Trade Mark, also available from Röhm).
3) Polymers of methacrylate esters containing trimethylaminoethyl cationic ester groups and other neutral ($C_{1-4}$)alkyl ester groups. Chloride ions may be present. Mean molecular weight 150,000. Viscosity (20° C.) 10 cP. Refractive Index 1.38. Density 0.815. Alkali number of 180 mg KOH per gram polymer (Eudragit E 100, Registered Trade Mark, also available from Röhm and hereinafter referred to a polymer C).

If desired the pharmaceutical composition may contain other additives, such as plasticizers and/or softeners preferably skin compatible tensides, e.g. to provide flexibility to the pharmaceutical composition, and/or to dissolve partially or totally compound A.

Examples of additives include:

1) Polyoxyethylene fatty alcohol ethers. The alcohol may e.g. be a $C_{12-18}$ alcohol. The HLB value may be e.g. from 10 to 18. A preferred example is polyoxyethylene-(10) oleyl ether. A suitable ether may have a viscosity (25° C.) of about 100 cP, a solidification point of about 16° C., an HLB value of 12.4 and an acid count maximum 1.0 (Brij 97 Registered Trade Mark available from Atlas Chemie, Germany).
2) Polyoxyethylene Sorbitan fatty acid esters. The fatty acid may be e.g. a $C_{12-18}$ fatty acid. The HLB value may be e.g. from 10 to 18. A preferred example is polyoxyethylene-(20) sorbitan monooleate, e.g. Tween 80, Registered Trade Mark available from Atlas Chemie, Germany.

3) Polyoxyethylene-(5-40) stearic acid esters, e.g. Myrj (Registered Trade Mark) available from Atlas Chemie, Germany.

4) Polyoxyethylene glycol fatty alcohol ethers, e.g. polyethylene glycol-(6-25) cetyl ether, glycerin polyethylene ricinoleate, glycerin polyethylene glycol stearate (Cremophor brand, Registered Trade Mark available from BASF Germany).

5) Polyoxyethylene glycols of MW from 200 to 600 Daltons, e.g. 300 or 400 Daltons.

6) Esters of poly(2-7)ethylene glycol glycerol ether having at least one hydroxyl group and an aliphatic ($C_{6-22}$) carboxylic acid, e.g. Polyethylene glycol-(7) glyceryl cocoate, e.g. Cetiol HE, Registered Trade Mark, from Henkel, Germany.

7) Adipic acid lower alkyl esters, e.g. di-n-butyl adipate and diisopropyl adipate.

8) Glycerin polyethylene glycol ricinoleate, e.g. Product of 35 moles ethylene oxide and castor oil, e.g. Brand Cremophor EL Registered Trade Mark, obtainable from BASF, Germany.

9) Triacetin-(1,2,3).

10) Fatty acid, e.g. a $C_{12-18}$ fatty acid.

11) Fatty alcohol, e.g. a $C_{12-18}$ fatty alcohol.

The amount and type of additive required may depend on a number of factors, e.g. the HLB value of the tenside and the flexibility of the pharmaceutical required. The amount of additive does not significantly influence the capability of the polyacrylate to form films. Generally the weight ratio of tenside to the polymer may be from about 1:10 to 5:1, e.g. 1:10 to 1:3.

Preferably, however, no such additive is present or is only present in an amount less than 1% by weight based on the total weight of the pharmaceutical composition.

The pharmaceutical composition may contain skin penetration promoters, e.g. 1-dodecylazacycloheptan-2-one (azone) and N,N-diethyl-m-toluamide (DEET).

The amount and type of skin penetration promoter, and/or additives present may depend on a number of factors. Generally the weight ratio of skin penetration promoting agent to hydrophilic polymer will be from about 1:1 to 1:10. Preferably the amount of tenside and/or skin penetration promoter may be from about 3 to about 50%, preferably 20 to 40% by weight of the pharmaceutical composition.

Preferably however no such additive is present or is only present in an amount less than 1% by weight of the pharmaceutical composition.

If desired the pharmaceutical composition may contain a hydrophobic elastomer, e.g. a synthetic resin. Such resins are conventional in the plaster art. Suitable resins may include non-swellable acrylate resins. These may if desired be adhesive. The weight ratio of polymer, e.g. hydrophilic polymer to resin may for example be from 1:0.5 to 1:10. The resin may contain modifiers, extenders, e.g. of softening point about 50 to 100° C. Such extenders may have adhesive or softening properties. Examples of such extenders may include resin acids, glyceryl and phthalate esters of resin acids.

A preferred pharmaceutical composition according to the invention comprises a) (S)-N-ethyl-3-[1-dimethylamino)ethyl]-N-methyl-phenyl-carbamate as compound A in free base form in an amount of 20 to 40 weight-%, b) polymethacrylate in an amount of 10 to 30% by weight c) acrylate copolymer in an amount of 40 to 60% by weight, and d) α-tocopherol in an amount of between 0.05 and 0.3% by weight wherein the total weight of the pharmaceutical composition is 100%.

In another aspect the present invention provides the use of an anti-oxidant to stabilize a pharmaceutical composition containing Compound A.

Before the finding by the present applicant that an anti-oxidant is necessary in compositions of this invention, it was hitherto thought unnecessary.

The applicant has found that an effective stabilising effect is surprisingly achieved when the anti-oxidant is selected from tocopherol, esters thereof, e.g. tocopherol acetate, ascorbyl palmitate, ascorbic acid, butylhydroxytoluene, butylhydroxyanisole or propyl gallate, preferably α-tocopherol or ascorbyl palmitate. The antioxidant may be conveniently present in an amount of from about 0.01 to about 0.5%, e.g. 0.05 to 0.20, e.g. 0.15%, more particularly 0.1% by weight based on the total weight of the pharmaceutical composition.

Pharmaceutical compositions of the invention produced in analogous manner to example 1 described hereinafter containing 0.1% tocopherol show for Example only 1.3% degradation products compared to 4.46% degradation products in equivalent compositions not containing tocopherol in 2 month stress tests at 60° C. Pharmaceutical compositions of the invention in analogous manner to example 1 described hereinafter containing 0.15% tocopherol show for example only 0.25% degradation products compared to 1.09% degradation products in compositions not containing tocopherol in 3 month stress tests at 40° C. at 75% room humidity.

The pharmaceutical composition of the invention is preferably used for transdermal application.

In another aspect of the invention there is provided a transdermal device for administering a Compound A which comprises a pharmaceutical composition containing Compound A, a backing layer providing support for the pharmaceutical composition, an adhesive for fixing the pharmaceutical composition to the backing layer and a release-liner releasably contacting said adhesive.

The pharmaceutical composition may be conveniently contained in a discrete thin layer, the upper and lower surfaces of which may be coated in a layer of adhesive the surface of which in turn provide backing layer and release-liner contacting surfaces.

The pharmaceutical composition contained in the discrete layer may comprise the Compound A and other excipients in a polymer matrix, the polymer matrix therefor being provided by the diluent or carrier aforementioned. If desired Compound A may be dispersed throughout, or dissolved in, said polymer matrix.

The transdermal device may alternatively be of a more simple construction wherein the polymer matrix containing the pharmaceutical composition additionally comprises an adhesive. In such a simple construction there is no need for the layers of the aforementioned adhesive in order to fix and releasably fix respectively the backing layer and release-liner as the polymer matrix containing the Compound A is self adhesive.

The thickness of the pharmaceutical composition layer in a transdermal device may be in the order of from 20 to 100 μm, more preferably 60 to 100.

The backing layer is preferably made of poly(ethylene terephthalate) PET foil. The backing layer should be thick enough to resist wrinkling which may arise upon prolonged periods in storage and through the movement of a subject's skin. Typically, the backing layer is, e.g. from approximately 10 $\mu$m to 15 $\mu$m, in thickness.

In a preferred embodiment, the backing layer is a double layer which consists of a PET layer as aforementioned and an EVA layer, e.g. Scotch Pack 1012.

The release-liner may be a disposable element which serves to protect the pharmaceutical composition prior to its application. Typically the release-liner is produced from a material impermeable to compound A, and adhesive. This release-liner may be easily stripped away from the adhesive. A preferred release-liner is made of poly(ethylene terephthalate) PET foil. A release-liner, e.g. of about 50 to 250 $\mu$m, e.g. 100 $\mu$m thickness PET film, may be applied over the pharmaceutical composition.

The release liner may be silicone-coated. Said coating is preferably formed of any fluorosilicone compound which is conventionally used in the art, e.g a polyfluoroalkylsiloxane.

It is particularly preferred to employ such a fluorosilicone coating when the adhesive used to affix the pharmaceutical composition to the release liner is not itself a silicone adhesive.

The adhesive may be chosen from any adhesive suitable for skin contact and is preferably an adhesive in which Compound A dissolves at least partly. Preferably the adhesive is a contact adhesive which is pressure sensitive. Preferred adhesive are chosen from amine-resistant silicone pressure sensitive adhesives known in the art, for example the BIO-PSA adhesives produced by Dow Coming Corporation, in particular BIO-PSA Q7-4302.

In a very simple construction of the transdermal device, the adhesive may in fact be the polymer of the polymer matrix.

In a further embodiment, the invention provides a transdermal device comprising a backing layer, a layer comprising compound A in a polymer matrix, a release-liner and, disposed between the layer comprising compound A in a polymer matrix and the release liner, a discrete layer of adhesive material for releasably fixing said transdermal device to patients skin.

Preferably, the adhesive material is a silicone adhesive chosen from amine-resistant silicone pressure sensitive adhesives as hereinabove described.

Typically, a transdermal device of said further embodiment comprises:

a) a polymethacrylate backing layer b) Compound A in free base form in an acrylate copolymer c) a BIO-PSA Q7-4302 silicone adhesive layer d) a release-liner.

Preferably, said further embodiment also comprises silicone oil, e.g. silicone oil Q7-9120 from Dow Coming Corporation, in an amount of 0.1 to 5% by weight, e.g. 1%. The backing layer thickness is preferably from 10 to 50 $\mu$m, e.g. 23 $\mu$m, and has preferably a round shape.

In general transdermal devices of the invention may be produced in a simple manner. A solvent-evaporation process may be used for said compositions. Thus all the ingredients of the pharmaceutical composition may be mixed in a solvent, e.g. acetone, ethylacetate or hexane, and cast onto a substrate which may act as the backing layer or the release-liner.

The transdermal device aforementioned may be conveniently formed in continuous sheets and may be cut into patches of any desirable size or configuration before use. However, the patches so-formed may expose the pharmaceutical composition-containing layer of the laminate to the atmosphere at the outer edges of the patch.

In an alternative embodiment, however, a transdermal device is provided wherein in the patches formed therefrom, the pharmaceutical composition is not exposed to the atmosphere during storage or during application. Such patches further reduce the likelihood of the Compound A being exposed to oxidative influences. The transdermal device may comprise, e.g. a continuous backing layer, a continuous release-liner and located there-between, in discrete portions, a pharmaceutical composition portion, the backing layer being configured such that it may be releasably fixed with an adhesive to the release-liner so to seal said pharmaceutical composition in a pocket defined by the inner surface of the backing layer and inner surface of the release-liner. This embodiment may be conveniently referred to as a cover patch.

The pocket described hereinabove is preferably filled with an adhesive so as to encapsulate completely the discrete portion of pharmaceutical composition. Preferably the adhesive is a silicone pressure sensitive adhesive as described hereinabove.

It is an optional feature of all the transdermal devices described hereinabove that they comprise a layer of adhesive between the pharmaceutical composition and the release liner. This, has the primary function of fixing the release liner in contact with the remainder of the device thus protecting the pharmaceutical composition before use. However, if the adhesive is a silicone adhesive, then the layer may additionally act as a membrane through which the Compound A may pass at a controlled rate into the patient through the skin. Without wishing to be limited to a particular theory, it is suggested that the Compound A, dispersed throughout the polymer matrix exhibits little tendency to migrate into the silicone adhesive layer during storage. Accordingly, there is relatively low concentration of Compound A in the silicone layer. In use, the subjects skin, however, may display a much higher affinity for Compound A than the silicone layer and the initial low concentration of Compound A in the silicone layer passes into the subject's body. The silicone layer surprisingly prevents the subject from receiving a sudden high dose of Compound A upon application of the device and instead promotes a gradual increase of concentration in the subject.

The cover patch transdermal device may conveniently be formed as a continuous sheet or webbing and may be cut, or torn along a frangible area dividing each device, into patches before use although such devices may be provided as discrete patches.

The transdermal devices of the invention in general have, for example an effective contact area of pharmaceutical composition on the skin of from about 1 to about 80 square centimeters, preferably about 10 square centimetres, and are intended to be applied at intervals of about once every 1 to 7 days, preferably 1–3 days. Compound A is well tolerated at a dose of 36 mg in free base form in up to 80 $cm^2$ of patches according to the invention containing 36 mg compound A from which 12 mg was absorbed. Compound A may, for example be administered at a dose of 8 mg in a patch of ca. 10 $cm^2$, once every day. The patch may be applied, for example on the abdomen, thigh, behind an ear, or on a shoulder or upper arm.

The pharmaceutical composition, optionally formed as a transdermal device, of the present invention are useful for the same indications as for known compositions containing compound A. The exact amounts of compound A to be administered may depend on a number of factors, e.g. the drug release characteristics of the compositions, the drug penetration rate observed in vitro and in vivo tests, the duration of action required, the form of compound A, and for transdermal compositions the size of the skin contact area, and the part of the body to which the unit is fixed. The amount of and, e.g. area of the composition etc. may be determined by routine bioavailability tests comparing the blood levels of active agents after administration of compound A in a composition according to the invention to intact skin and blood levels of Compound A observed after oral administration of a therapeutically effective dose of the compound.

Orally, the Compound A is well tolerated at an initial dose of 1.5 mg twice a day orally and the dose may be stepped up to 3 mg twice daily in week 2. Higher dosages are possible, for example 4.5 mg twice daily and even 6 mg twice daily. Tolerability is seen to be even better for the transdermal device, wherein 24 mg were absorbed in 24 hours.

The following example illustrates the invention.

EXAMPLE 1

A composition is prepared consisting of the following components (by weight)

| | (I) | (II) |
|---|---|---|
| Compound A | 30% | 30% |
| Polymer | 20% (A) | 20% (D) |
| Methacrylate | 49.85% (B) | 49.85% (C) |
| α-tocopherol | 0.15% | 0.15% |

The components are added to ethyl acetate and mixed to give a viscous mass. The mass is spread onto a 100 μm transparent PET foil to produce a film 60 μm thick. A 15 μm thick PET foil release-liner is applied onto the dried mass. The patch is cut up into patches 10, 20, 30 or 40 $cm^2$ in area.

The liner is removed before application to the skin.

The compositions and devices of this invention provide storage stable systems. Insignificant degradation is detected after storage of up to 6 months at room temperature.

EXAMPLE 2

A composition is prepared according to Example 1 with Ascorbyl-palmitate instead of α-tocopherol. Insignificant amounts of degradation products are detected after storage of at least four months at room temperature.

EXAMPLE 3

A composition is prepared according to Example 1 with a mixture of Ascorbyl-palmitate and α-tocopherol instead of α-tocopherol alone. Insignificant amounts of degradation products are detected after storage of at least four months at room temperature.

EXAMPLE 4

A two-parts composition is prepared consisting of the following components

-continued

| | Composition per unit (10 $cm^2$) | |
|---|---|---|
| Compound A | 18 mg | 30% |
| Polymer | 29.94 mg | 49.85% |
| Methacrylate | 12 mg | 20% |
| α-tocopherol | 0.06 | 0.1% |
| Total 1st part (area weight 60 mg/10 $cm^2$) | 70 mg | 100% |
| and | | |
| Bio-PSA Q7-4302 | 29.67 mg | 98.9% |
| Silicone oil Q7-9120 | 0.3 mg | 1.0% |
| α-tocopherol | 0.03 mg | 0.1% |
| Total 2nd part (area weight 30 mg/10 $cm^2$) | 30 mg | 100% |

The two parts are then put together in the form of a patch.

What is claimed is:

1. A pharmaceutical composition comprising 1 to 40 weight percent of (S)-N-ethyl-3-[(1-dimethylamino)ethyl]-N-methylphenyl carbamate in the form of a free base or acid addition salt, 0.01 to 0.5 weight percent of an antioxidant, and a diluent or carrier, wherein the weight percents are based on the total weight of the pharmaceutical composition.

2. The composition according to claim 1 wherein the antioxidant is selected from the group consisting of tocopherol, esters of tocopherol, ascorbic acid, esters of ascorbic acid, butylhydroxytoluene, butylhydroxyanisole, propyl gallate, and combinations thereof.

3. The composition according to claim 2 wherein the antioxidant is α-tocopherol or ascorbyl palmitate.

4. The composition according to claim 1 wherein the antioxidant is present in an amount of from 0.05 to 0.2 weight percent.

5. The composition according to claim 4 wherein the antioxidant is present in an amount of from 0.1 to 0.15 weight percent.

6. A pharmaceutical composition comprising 7 to 40 weight percent of (S)-N-ethyl-3-[(1-dimethylamino)ethyl]-N-methylphenyl carbamate in the form of a free base; 10 to 30 weight percent of polymethacrylate or acid addition salt; 0.05 to 0.3 weight percent of α-tocopherol, wherein the weight percents are based on the total weight of the composition.

7. A transdermal device comprising a pharmaceutical composition comprising 1 to 40 weight percent of (S)-N-ethyl-3-[(1-dimethylamino)ethyl]-N-methylphenyl carbarnate in the form of a free base or acid addition salt, 0.01 to 0.5 weight percent of an antioxidant, and a diluent or carrier, wherein the weight percents are based on the total weight of the pharmaceutical composition.

8. The transdermal device according to claim 7 further comprising an antioxidant; a backing layer providing support for the pharmaceutical composition; an adhesive for contacting and fixing the pharmaceutical composition to the backing layer; and a release liner releasably contacting said adhesive.

9. The transdermal device according to claim 7 comprising a backing layer; a layer comprising (S)-N-ethyl-3-[(1-dimethylamino)ethyl]-N-methylphenyl carbamate and an antioxidant in a polymer matrix; a release liner; and an adhesive layer between the layer comprising (S)-N-ethyl-3-[(1-dimethylamino)ethyl]-N-methylphenyl carbamate in a polymer matrix and the release liner, wherein the adhesive layer releasably fixes the transdermal device to a patients skin.

* * * * *

UNITED STATES PATENT AND TRADEMARK OFFICE

CERTIFICATE OF CORRECTION

PATENT NO. : 6,316,023 B1
DATED : November 13, 2002
INVENTOR(S) : Asmussen et al.

It is certified that error appears in the above-identified patent and that said Letters Patent is hereby corrected as shown below:

Column 8,
Line 1, should read -- A pharmaceutical compostion comprising 20 to 40 --.
Line 3, should read -- Ethyl-3-[(1dimethylamino)ethyl]-N-methylphenyl carba- --.
Line 4, should read --mate in the form of a free base or acid addition salt, 0.01 to --.

Signed and Sealed this

Twenty-fifth Day of March, 2003

JAMES E. ROGAN
*Director of the United States Patent and Trademark Office*